Figure 1:
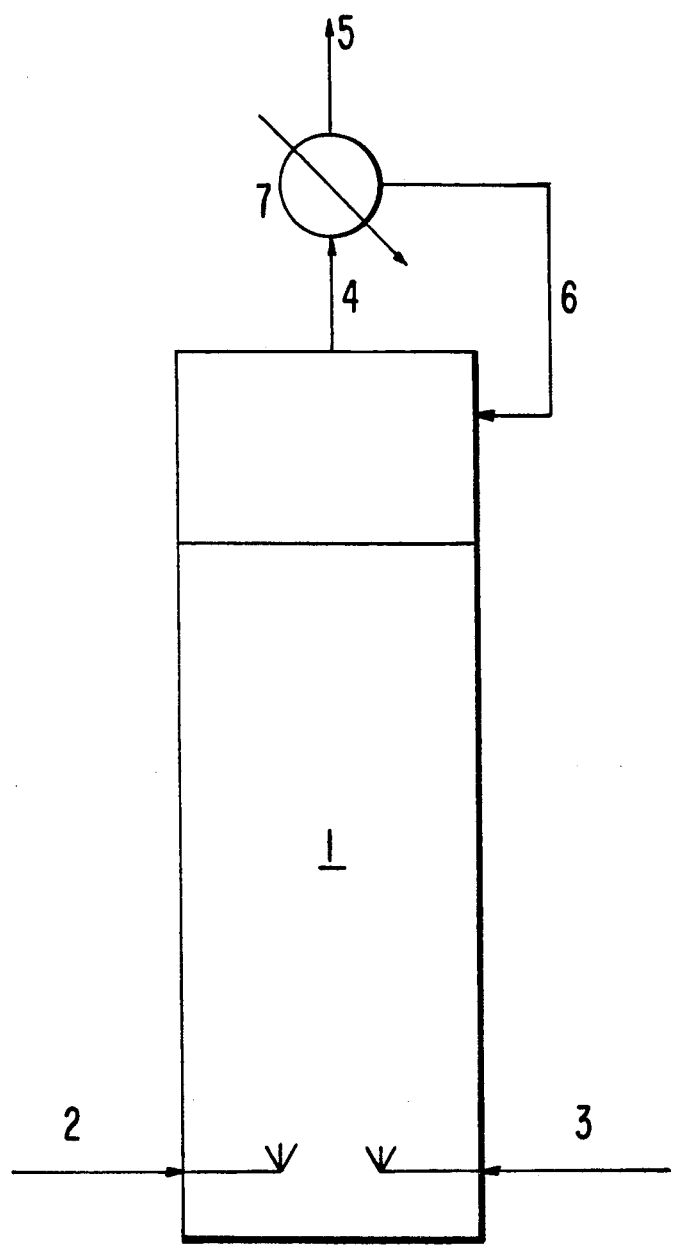

United States Patent [19]

Walraevens et al.

[11] Patent Number: 5,159,126

[45] Date of Patent: * Oct. 27, 1992

[54] PROCESS FOR THE MANUFACTURE OF 1-CHLORO-1,1-DIFLUOROETHANE

[75] Inventors: René Walraevens; James Franklin, both of Brussels; Jean-Marie Yernaux, Rixensart, all of Belgium

[73] Assignee: Solvay S.A., Brussels, Belgium

[*] Notice: The portion of the term of this patent subsequent to Apr. 16, 2008 has been disclaimed.

[21] Appl. No.: 621,891

[22] Filed: Dec. 4, 1990

Related U.S. Application Data

[63] Continuation of Ser. No. 491,065, Mar. 9, 1990, Pat. No. 5,008,474, which is a continuation of Ser. No. 672,177, Nov. 15, 1984, abandoned, which is a continuation of Ser. No. 572,132, Jan. 19, 1984, abandoned, which is a continuation of Ser. No. 407,078, Aug. 11, 1982, abandoned, which is a continuation of Ser. No. 268,702, Jun. 1, 1981, abandoned, which is a continuation of Ser. No. 824,320, Aug. 12, 1977, abandoned.

[51] Int. Cl.⁵ .................... C07C 17/20; C07C 19/02

[52] U.S. Cl. .................... 570/168; 570/165; 570/166; 570/167; 570/169

[58] Field of Search .............. 570/168, 165, 166, 167, 570/169

[56] References Cited

U.S. PATENT DOCUMENTS

| 2,452,975 | 11/1948 | Whalley | 570/168 |
| 5,008,474 | 4/1991 | Wairaevens et al. | 570/165 |

FOREIGN PATENT DOCUMENTS 39086 10/1972 Japan ........................ 570/168

OTHER PUBLICATIONS

Translation of Kureha (PTO 90-396).

Primary Examiner—Joseph E. Evans
Attorney, Agent, or Firm—Willian Brinks Olds Hofer Gilson & Lione

[57] ABSTRACT

1-Chloro-1,1-difluoroethane is prepared by reacting hydrogen fluoride with vinylidene chloride, in a liquid medium containing preferably at least 40 mol % 1,1-dichloro-1-fluoroethane.

9 Claims, 2 Drawing Sheets

PROCESS FOR THE MANUFACTURE OF 1-CHLORO-1,1-DIFLUOROETHANE

This is a continuation of application Ser. No. 07/491,065 filed Mar. 9, 1990, now U.S. Pat. No. 5,008,474, which in turn is a continuation of application Ser. No. 07/672,177 filed Nov. 15, 1984 which in turn is a continuation of application Ser. No. 06/572,132 filed on Jan. 19, 1984 which in turn is a continuation of application Ser. No. 06/407,078 filed on Aug. 11, 1982 which in turn is a continuation of application Ser. No. 06/268,702 filed on Jun. 1, 1981 which in turn is a continuation of application Ser. No. 05/824,320 filed on Aug. 12, 1977, all except Ser. No. 07/491,065 have been abandoned.

The present invention relates to a process for the manufacture of 1-chloro-1,1-difluoroethane from vinylidene chloride by reaction with hydrogen fluoride, if appropriate in the presence of a catalyst.

1-Chloro-1,1-difluoroethane is an intermediate product of the synthesis of vinylidene fluoride, which is itself used for the manufacture of polymers.

The known processes of fluorination of vinylidene chloride by means of hydrogen fluoride have hitherto not made it possible to obtain high yields of 1-chloro-1,1-difluoroethane. In fact, under mild conditions, only the addition product, namely 1,1-dichloro-1-fluoroethane can be obtained. Furthermore, if very active catalysts, high molecular ratios of hydrogen fluoride: vinylidene chloride, high temperatures, or several of these conditions simultaneously are used, undesired products such as 1,1,1-trifluoroethane, as well as a large amount of oligomers, are obtained.

To favour the formation of 1-chloro-1,1-difluoroethane, it has been proposed, in Japanese Patent Application 39,086/72 filed on Aug. 31st, 1964 in the name of Kureha Chemical Ind. Co., to carry out the reaction in the presence of tin tetrachloride, with a molar ratio of hydrogen fluoride: vinylidene chloride greater than 4, and at a temperature above 60° C. However, this process does not make it possible completely to avoid the formation of undesirable by-products. Thus, in this process, a substantial formation of 1,1,1-trifluoroethane is observed, in spite of a very low degree of fixing of the hydrogen fluoride.

There has now been found, in accordance with the present invention a process for the manufacture of 1-chloro-1,1-difluoroethane by hydrofluorination of vinylidene chloride which does not exhibit the disadvantages, mentioned above, of the known processes.

Accordingly, the present invention relates to a process for the manufacture of 1-chloro-1,1-difluoroethane by reaction of hydrogen fluoride with vinylidene chloride, in which the reaction is carried out in a liquid medium containing 1,1-dichloro-1-fluoroethane.

The number of mols of 1,1-dichloro-1-fluoroethane present in the liquid medium is at least 40 mol. % preferably greater than 40% relative to the total number of mols of organic compounds participating in the reaction and present in the liquid medium. The best results are obtained when this amount is at least 60 mol % greater than 60%. However, a beneficial effect is observed even from 20% onwards. By organic compounds participating in the reaction there are understood vinylidene chloride, 1,1-dichloro-1-fluoroethane, 1-chloro-1,1-difluoroethane and all the by-products of the reaction.

In addition to 1,1-dichloro-1-fluoroethane, the liquid medium in particular contains vinylidene chloride and the products of the reaction; it can also possibly contain one or more liquid solvents which are inert under the reaction conditions and have a boiling point above that of 1-chloro-1,1-difluoroethane under the pressure conditions of the reaction. The content of vinylidene chloride in the liquid medium preferably does not exceed 50 mol % relative to the total number of mols of organic compounds participating in the reaction and present in the medium. The best results are obtained when it does not exceed 30%. In fact, if the vinylidene chloride content is higher, the formation of large amounts of oligomeric by-products is observed.

The amount of 1-chloro-1,1-difluoroethane in the liquid medium preferably does not exceed 50 mol % relative to the total number of mols of organic compounds participating in the reaction and present in the liquid medium. The best results are obtained if it does not exceed 30%. In fact, if the content of 1-chloro-1,1-difluoroethane is higher, the formation of undesirable highly fluorinated products is observed.

The liquid medium furthermore contains hydrogen fluoride as well as, optionally, various other additives and, in particular, catalysts.

As catalysts it is possible to use any hydrofluorination catalyst which favours the replacement of a chlorine atom by a fluorine atom. Catalysts which simultaneously favour the addition of the hydrogen fluoride to a double bond and the replacement of a chlorine atom by a fluorine atom are very suitable. Amongst the catalysts which can be used there may be mentioned the compounds of the elements chosen from amongst the elements of groups IIIa and b, IVa and b, Va and b, VIa and b, VIIb and VIII of the periodic table of the elements and more particularly from amongst lanthanum, boron, aluminium, gallium, titanium, tin, vanadium, bismuth, arsenic, antimony, chromium, sulphur, manganese, iron, cobalt and nickel. Titanium, tin, vanadium, bismuth, arsenic, antimony, chromium compounds are generally used. The tin compounds are particularly suitable The compounds used are preferably the halides, such as the chlorides and the fluorides, as well as the oxides and the oxyhalides and preferably the oxychlorides and oxyfluorides Tin tetrachloride has proved particularly valuable.

The catalyst or catalysts are usually employed at the rate of 0.001 to 5 and preferably of 0.01 to 2 mols per kg of liquid medium.

In order to maintain a sufficient content of 1,1-dichloro-1-fluoroethane in the liquid medium, a simple means consists of continuously withdrawing the 1-chloro-1,1-difluoroethane from the reaction medium so that the latter does not accumulate in the reactor. The 1-chloro-1,1-difluoroethane can be removed from the liquid medium in various ways. Thus, it is possible continuously to take a part of the liquid medium and to subject it to a separation in order separately to collect 1-chloro-1,1-difluoroethane and recycle, to the reactor, a liquid enriched in 1,1-dichloro-1-fluoroethane. It is also possible, according to a preferred embodiment of the invention, to use a temperature and a pressure such that the 1-chloro-1,1-difluoroethane continuously leaves the liquid medium in the form of a gas. In this latter case, it is also possible simultaneously to withdraw a part of the liquid medium and subject it to a separation as described above.

The reaction temperature is generally chosen to be between 30° and 180° C. and preferably between 40° and 160° C. The reaction pressure is chosen so as to maintain the reaction medium in the liquid form. It is most commonly between 2 and 80 kg/cm$^2$ and varies according to the temperature of the reaction medium. If it is desired continuously to withdraw a part of the liquid phase in order to remove the 1-chloro-1,1-difluoroethane therefrom, it is preferable to use high pressures, for example between 5 and 80 kg/cm$^2$. On the other hand if, according to the preferred embodiment of the invention, it is desired to withdraw the 1-chloro-1,1-difluoroethane in the gaseous form from the reaction medium, lower pressures, for example between 2 and 50 kg/cm$^2$, are used. In this latter case, pressures of between 3 and 30 kg/cm$^2$ have proved advantageous.

According to the preferred embodiment of the invention, the reaction temperature and pressure are chosen so as, on the one hand, to ensure that the reaction medium is kept in the liquid phase and, on the other hand, to allow the 1-chloro-1,1-difluoroethane to leave the reaction medium in the gaseous form, whilst maintaining the vinylidene chloride, 1,1-dichloro-1-fluoroethane and hydrogen fluoride in the liquid form.

The molar ratio of hydrogen fluoride: vinylidene chloride is generally chosen to be above 1.5. Most frequently, molar ratios of between 1.5 and 4, and preferably between 1.75 and 3.7, are used. The rates of introduction of the reactants are so regulated as to maintain the desired proportions for the compounds present in the reaction medium and especially so as to avoid the accumulation of vinylidene chloride in the liquid medium.

The reaction can be carried out in various types of reactors which are in themselves known. Thus it is possible to introduce the hydrogen fluoride and vinylidene chloride in parallel at the bottom of a vertical reactor containing 1,1-dichloro-1-fluoroethane. It is also possible to cause hydrogen fluoride and vinylidene chloride to flow through the reactor in counter-current.

The reactor is usually made from materials which are resistant to pressure and to hydrogen fluoride. In general, reactors made of steel, stainless steel, nickel, copper or an alloy containing chromium, chromium and nickel, nickel and copper or even molybdenum are used. Alloys such as MONEL, INCONEL and HASTELLOY are very suitable. It is also possible to use reactors equipped with a lining of an inert metal or alloy, or coated with a layer of a resin which is inert under the reaction conditions, such as, for example, phenoplasts or fluorinated resins.

The reactors are advantageously equipped with devices which are in themselves known and make it possible to improve the contact between the hydrogen fluoride and the reactant. It is thus possible to provide stirrers in the reactor or to provide means of introducing the reactants which allow efficient dispersion of the latter in the reaction medium.

One of the reactants, or both reactants and/or the catalyst can optionally be introduced at several spaced-out points of the reactor. Thus it is possible and valuable to equip the reactor with several means of introducing the vinylidene chloride.

The reaction can be carried out in a single reactor or in several reactors arranged in series. In this case, it is possible to provide various means of introducing the reactants and the catalyst. The two reactants can be introduced into one and the same reactor, the catalyst being divided amongst all the reactors. It is also possible to introduce at least one of the two reactants into each of the reactors. It is also possible to use two reactors respectively fed with each of the reactants, the two mixtures formed in each of the reactors flowing in counter-current.

When the 1-chloro-1,1-difluoroethane leaves the reaction medium in the gaseous form, a gas phase which furthermore contains hydrogen chloride, volatile by-products such as 1,1,1-trifluoroethane as well as a little hydrogen fluoride, 1,1-dichloro-1-fluoroethane, vinylidene chloride and possibly 1,1,1-trichloroethane as a by-product of the reaction is collected. This mixture can be subjected to one or more separations so as to collect the 1-chloro-1,1-difluoroethane which is the product of the reaction, whilst the hydrogen fluoride, 1,1-dichloro-1-fluoroethane, vinylidene chloride and any 1,1,1-trichloroethane can be recycled to the reactor.

It is thus possible to subject the gas mixture coming from the reactor to a fractional distillation so as to separate the hydrogen chloride from a mixture containing the hydrogen fluoride and the organic compounds. This mixture can then be decanted to separate the hydrogen fluoride from the organic phase, the latter being subjected to several successive distillations which make it possible to collect the 1-chloro-1,1-difluoroethane, which is the reaction product, and the 1,1-dichloro-1-fluoroethane as well as the vinylidene chloride, which are recycled to the reactor at the same time as the unconverted hydrogen fluoride.

Figure 2:
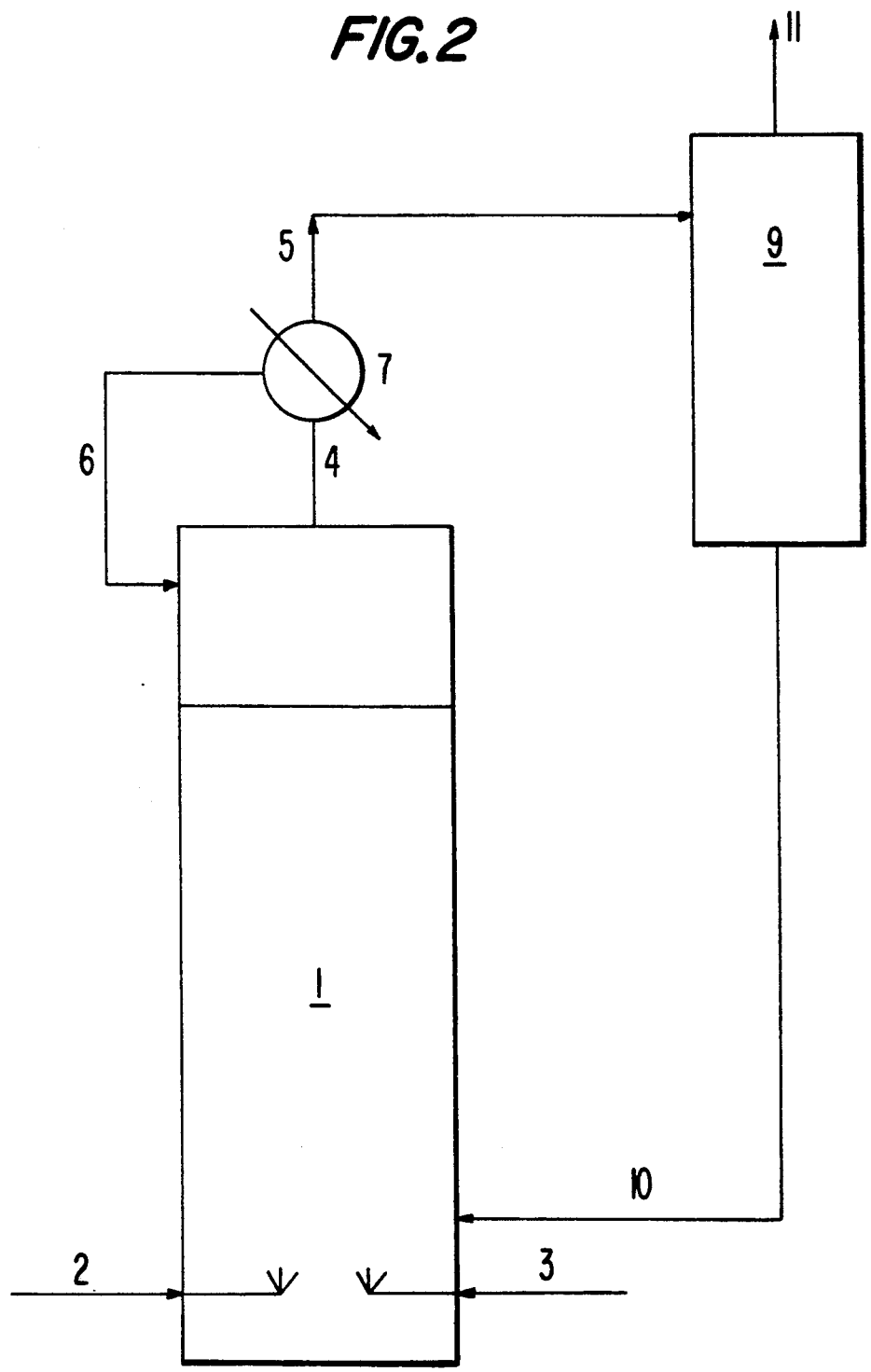

The attached FIGS. 1 and 2 schematically represent valuable embodiments of the process according to the present invention.

According to the diagram in FIG. 1, hydrogen fluoride is introduced into a reactor 1, containing 1,1-dichloro-1-fluoroethane in the liquid phase, through line 2 and vinylidene chloride through line 3. The gases which have left the reactor through line 4 pass into a condenser 7 from which a liquid phase is withdrawn, which is recycled through line 6 to the reactor 1, and a gaseous phase is withdrawn through line 5. The gaseous phase which is withdrawn at 5 contains principally hydrogen chloride, 1-chloro-1,1-difluoroethane, 1,1,1-trifluoroethane as a by-product and possibly also a little hydrogen fluoride, 1,1-dichloro-1-fluoroethane and vinylidene chloride.

In the process represented in FIG. 2, hydrogen fluoride is introduced into a reactor 1, containing 1,1-dichloro-1-fluoroethane in the liquid phase, through line 2 and vinylidene chloride through line 3. The gases which have left the reactor through line 4 pass into a condenser 7, from which a liquid phase is withdrawn, which is recycled through line 6 to the reactor 1, and a gas phase containing hydrogen chloride, 1,1,1-trifluoroethane, 1-chloro-1,1-difluoroethane and a little hydrogen fluoride, 1,1-dichloro-1-fluoroethane and vinylidene chloride is also withdrawn. This gaseous phase is withdrawn through line 5 and passed into a separation zone 9 from which hydrogen chloride, 1,1,1-trifluoroethane and 1-chloro-1,1-difluoroethane are withdrawn at 11 and a mixture containing hydrogen fluoride, vinylidene chloride and 1,1-dichloro-1-fluoroethane is withdrawn at 10. The separation zone 9 can in particular be a distillation zone. It can also be replaced by an assembly of separation apparatuses comprising, for example, distillation columns, scrubbers and decanters so arranged as to separate the gaseous mixture into all its constituents.

The process according to the present invention has proved particularly valuable. In fact, it makes it possible substantially to reduce the formation of oligomers. Furthermore, very little 1,1,1-trifluoroethane is formed, in spite of a high degree of utilisation of the hydrogen fluoride. The process of the invention thus makes it possible to achieve very high yields of 1-chloro-1,1-difluoroethane. The latter is advantageously used in the manufacture, by dehydrochlorination, of vinylidene fluoride, which is a monomer used for the preparation of polymers having high chemical resistance and high heat resistance.

Example 2 which follows, and which is in no way limiting in character, shows the remarkable results obtained in accordance with an embodiment of the invention. Example 1R is given by way of comparison.

EXAMPLE 1 (R)

By way of comparison, an experiment was carried out discontinuously, in a liquid medium which at the start of the reaction only contained vinylidene chloride, hydrogen fluoride and catalyst.

The experiment was carried out at 60° C. in a 3.5 l stainless steel reactor initially containing 5.16 mols of vinylidene chloride, 16.05 mols of hydrogen fluoride and 0.25 mol of tin tetrachloride. The reactor is equipped with a stirrer rotating at 290 revolutions per minute and surmounted by a condenser, the outlet temperature of which is about −20° C. The pressure in the reactor is kept at 5.4 atmospheres absolute which, in view of the formation of hydrogen chloride during the reaction, necessitates releasing a part of the contents of the reactor. The organic gases released, as well as the organic compounds present in the reactor at the end of the experiment, are collected and analysed. The analysis of all the products obtained after 1 hour 30 minutes of reaction is given in Table I below:

TABLE I

| Experiment | 1 R total organic compounds (mols) | mol % |
|---|---|---|
| 1,1,1-trifluoroethane | 0.111 | 2.1 |
| 1-chloro-1,1-difluoroethane | 1.377 | 26.7 |
| 1,1-dichloro-1-fluoroethane | 3.339 | 64.8 |
| vinylidene chloride | 0.218 | 4.2 |
| 1,1,1-trichloroethane | 0.041 | 0.8 |
| oligomers (equivalents of ethane derivatives) | 0.070 | 1.4 |

The degree of conversion of the vinylidene chloride is 95.8%.

The molar ratio of 1,1,1-trifluoroethane:1-chloro-1,1-difluoroethane is 0.080.

The degree of conversion of the vinylidene chloride to oligomers is 1.4%.

The oligomers were determined by vapour phase chromatography and identified by mass spectrometry. They consist of molecules of the formula

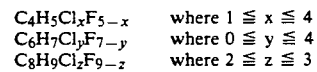

$C_4H_5Cl_xF_{5-x}$    where $1 \leq x \leq 4$
$C_6H_7Cl_yF_{7-y}$    where $0 \leq y \leq 4$
$C_8H_9Cl_zF_{9-z}$    where $2 \leq z \leq 3$

EXAMPLE 2

The experiments below were carried out in accordance with the invention, in a device similar to that shown in FIG. 1.

2 l of a liquid bottom layer are placed in the reactor, having a volume of 3.5 l, which is made of stainless steel. Two tubes dipping to the bottom of the reactor make it possible to introduce hydrogen fluoride and vinylidene chloride. The reactor is equipped with a stirrer turning at 290 revolutions per minute and is surmounted by a condenser.

The working conditions and the results obtained are shown in Table II below.

TABLE II

| | | EXPERIMENT No. 2 | 3 | 4 |
|---|---|---|---|---|
| Experimental conditions | | | | |
| Reaction temperature | °C. | 60 | 60 | 60 |
| Temperature at condenser outlet | °C. | 40–50 | 60 | 60 |
| Pressure | atmospheres absolute | 5.4 | 7.0 | 7.0 |
| Catalyst content | mol/kg of liquid medium | 0.5 | 0.5 | 0.5 |
| Volume of the liquid medium | l | 2 | 2 | 2 |
| Composition of the liquid medium | | | | |
| 1,1-dichloro-1-fluoroethane | mol % of | 84.2 | 76.01 | 80.3 |
| 1-chloro-1,1-difluoroethane | organic | 10.1 | 12.6 | 14.1 |
| vinylidene chloride | compounds | 3.2 | 8.13 | 2.0 |
| Feed of reactants | | | | |
| Vinylidene chloride | mol/hour | 6.37 | 6.51 | 6.16 |
| Hydrogen fluoride | mol/hour | 18.83 | 18.25 | 17.73 |
| Hydrogen fluoride: vinylidene chloride | mol/mol | 2.9 | 2.8 | 2.9 |
| Products formed | | | | |
| 1,1,1-trifluoroethane | mol/hour | 0.060 | 0.100 | 0.157 |
| 1-chloro-1,1-difluoroethane | | 5.279 | 5.224 | 5.252 |
| 1,1-dichloro-1-fluoroethane | | 0.983 | 1.154 | 0.732 |
| vinylidene chloride | | 0.022 | 0.023 | 0.004 |
| 1,1,1-trichloroethane | | 0.004 | 0.005 | 0.007 |
| oligomers (equivalent of ethane derivatives | | 0.027 | 0.007 | 0.011 |
| Degree of conversion of the vinylidene chloride | mol % | 99.7 | 99.6 | 99.9 |
| Degree of conversion of the vinylidene chloride to oligomers | | 0.4 | 0.1 | 0.2 |
| Degree of conversion of the vinylidene chloride to 1,1,1-trifluoroethane | | 0.9 | 1.5 | 2.5 |
| Selectivity in respect of 1-chloro-1,1- | | 83.1 | 80.5 | 85.3 |

TABLE II-continued

| | EXPERIMENT No. | | |
|---|---|---|---|
| | 2 | 3 | 4 |
| difluoroethane | | | |
| Selectivity in respect of (1-chloro-1,1-difluoroethane + 1,1-dichloro-1-fluoroethane) | 98.6 | 98.3 | 97.2 |

Furthermore, comparison of Tables I and II shows that in experiments 2, 3 and 4, molar ratios of 1,1,1-trifluoroethane: 1-chloro-1,1-difluoroethane much lower (respectively 0.011, 0.019 and 0.029) than in the comparison experiment 1 R (0.080) are obtained. The formation of 1,1,1-trifluoroethane relative to the desired product is thus much less in the process of the invention than in the comparison process.

We claim:

1. Continuous process for the manufacture of 1-chloro-1,1-difluoroethane with substantially reduced formation of 1,1,1-trifluoroethane and oligomers by reacting hydrogen fluoride with vinylidene chloride, wherein the reaction is carried out in a liquid medium in the presence of a hydrofluorination catalyst which is a tin compound, comprising:

a.) maintaining in said liquid medium a content greater than 60 mol. % of 1,1-dichloro-1-fluoroethane, no more than 30 mol. % of 1-chloro-1,1-difluoroethane and no more than 30 mol. % of vinylidene chloride, all relative to the total number of moles of organic compounds participating in the reaction and present in said liquid medium;

b.) feeding into said liquid medium hydrogen fluoride and vinylidene chloride in a hydrogen fluoride/vinylidene chloride molar ratio above 1.5;

c.) maintaining the pressure between 2 and 50 kg/cm² and the temperature between 30° and 160° C. in order to allow the 1-chloro-1,1-difluoroethane to leave said liquid medium in the gaseous form;

d.) continuously withdrawing from said liquid medium a gaseous phase containing 1-chloro-1,1-difluoroethane;

e.) submitting said gaseous phase containing 1-chloro-1,1-difluoroethane, hydrogen chloride, 1,1,1-trifluoroethane, hydrogen fluoride, 1,1-dichloro-1-fluoroethane, vinylidene chloride and possibly 1,1,1-trichloroethane to one or more separations;

f.) collecting the 1-chloro-1,1-difluoroethane which is the product of the reaction; and g.) recycling hydrogen fluoride, 1,1-dichloro-1-fluoroethane and vinylidene chloride to the reactor.

2. Process according to claim 1 wherein the gaseous phase coming from the reactor is submitted to a fractional distillation to separate the hydrogen chloride from said gaseous phase so as to obtain a mixture containing hydrogen fluoride and organic compounds.

3. Process according to claim 1 wherein the gaseous phase coming from the reactor passes into a condenser in order to obtain a liquid phase which is recycled to the reactor and a gaseous mixture containing hydrogen chloride, 1,1,1-trifluoroethane, 1-chloro-1,1-difluoroethane, 1,1-dichloro-1-fluoroethane, vinylidene chloride and part of the hydrogen fluoride.

4. Process according to claim 1 wherein the gaseous phase coming from the reactor is separated in an assembly of separation apparatuses comprising distillation columns, scrubbers and decanters.

5. Process according to claim 1 wherein the reaction is carried out in a single reactor.

6. Process according to claim 1 wherein the reaction is carried out in several reactors arranged in series.

7. Process according to claim 1 wherein the reaction zone is equipped with several means for introducing the vinylidene chloride.

8. Process according to claim 6 wherein at least one of the reactant is introduced into each of the reactors.

9. Process according to claim 1 wherein the catalyst is a tin halide.

* * * * *